United States Patent [19]
Jenczewski et al.

[11] Patent Number: 5,414,154
[45] Date of Patent: May 9, 1995

[54] PHENOL WITH LOW LEVELS OF METHYLBENZOFURAN

[75] Inventors: Theodore J. Jenczewski, Midlothian; Lamberto Crescentini; James A. Kweeder, both of Chester, all of Va.

[73] Assignee: AlliedSignal Inc., Morris Township, Morris County, N.J.

[21] Appl. No.: 254,729

[22] Filed: Jun. 6, 1994

[51] Int. Cl.⁶ .................. C07C 37/68; C07C 37/70
[52] U.S. Cl. .................. 568/754; 568/383; 568/410; 568/449; 568/741; 568/742; 568/768; 568/798
[58] Field of Search ........... 568/754, 383, 768, 338, 568/410, 449, 741, 742, 798

[56] References Cited

U.S. PATENT DOCUMENTS

| | | | |
|---|---|---|---|
| 3,029,294 | 4/1962 | Keeble | 568/754 |
| 3,692,845 | 9/1972 | Cheema et al. | 568/754 |
| 3,810,946 | 5/1974 | Yeh et al. | 260/621 |
| 4,298,765 | 11/1981 | Cochran et al. | 568/754 |
| 4,634,796 | 1/1987 | Suciu et al. | 568/757 |
| 4,857,151 | 8/1989 | Suciu et al. | 203/82 |
| 5,064,507 | 11/1991 | O'Donnell et al. | 203/34 |

FOREIGN PATENT DOCUMENTS

| | | | |
|---|---|---|---|
| 1668952 | 11/1969 | Germany | 568/754 |
| 0134427 | 2/1979 | Germany | 568/754 |

OTHER PUBLICATIONS

"Solid Superacid Catalysts" by Makoto Misono and Toshio Okuhara, Chemtech, Nov. 1993, pp. 23–29.
"Sulphonic Acid Cation-Exchangers as Catalysts in the Refining of Phenol and Aromatic Hydrocarbons" by Kazimierz Zieborak and Wlodzimierz Ratajczak, Chemistry and Industry, Jul. 4, 1993, pp. 516–518.

*Primary Examiner*—Werren B. Lone
*Attorney, Agent, or Firm*—Roger H. Criss; Gus T. Hampilos; Melanie L. Brown

[57] ABSTRACT

A process for the reduction of methylbenzofuran (MBF) impurities in phenol obtained from the decomposition product of cumene hydroperoxide requires treating the phenol to reduce the level of acetol, contacting the phenol containing a low level of acetol with an acid resin at sufficient temperature and residence time to reduce the level of MBF by conversion to higher boiling compounds, then distilling the phenol to separate phenol from higher boiling compounds. The phenol may be treated in known ways, such as by treatment with an amine, to reduce the level of acetol. The phenol containing a low level of acetol is contacted with a strong acid resin to reduce the level MBF.

9 Claims, No Drawings

PHENOL WITH LOW LEVELS OF METHYLBENZOFURAN

BACKGROUND OF THE INVENTION

1. Field of the Invention

This invention relates to the production of high purity phenol, particularly to a process for reduction of levels of methylbenzofuran in phenol to obtain desired high purity.

2. Description of Related Art

Phenol may be produced from cumene by the oxidation of cumene to cumene hydroperoxide, followed by cleavage or decomposition of the hydroperoxide to phenol and acetone. The reaction product is introduced into a separation and recovery system wherein acetone is separated from remaining product by distillation. The remaining product is then further distilled to separate cumene. The cumene recovery column can be operated if desired to recover alpha-methylstyrene (AMS) with the cumene, or the product remaining from the cumene recovery column may be introduced into a crude AMS column to separate AMS from the remaining product. The remaining product is introduced into a phenol recovery column to separate phenol from remaining higher boiling constituents.

The phenol product obtained by fractional distillation includes many impurities including AMS, acetol (hydroxyacetone), acetophenone, cumylphenols and 2- and 3-methylbenzofuran (collectively or individually MBF). For certain purposes it is important to reduce such impurities to avoid problems with discoloration on aging or on sulfonation or on chlorination. Since MBF and phenol have similar volatility, MBF cannot be separated effectively by fractional distillation. Distillation in the presence of water, or steam stripping, has been disclosed in U.S. Pat. Nos. 5,064,507 and 4,857,151 to reduce the amount of MBF. Such steam stripping requires substantial expenditure of energy to produce the necessary amount of steam and the use of large distillation columns to accommodate the flow of the organic vapors and the added steam. Thus removal of MBF by steam stripping is expensive in terms of operating cost and capital investment. U.S. Pat. No. 3,810,946 discloses reduction of MBF impurities by heating phenol with hydrobromic or hydroiodic acid. Treatment with halogenated compounds, however, leads to problems with corrosion which adds substantially to the cost of materials of construction.

The need exists for an effective and economical process to reduce the level of MBF in phenol to obtain desired high purity phenol.

SUMMARY OF THE INVENTION

A process for the reduction of methylbenzofuran (MBF) impurities in phenol obtained from the decomposition product of cumene hydroperoxide requires treating the phenol to reduce the level of acetol, contacting the phenol containing a low level of acetol with an acid resin at sufficient temperature and residence time to reduce the level of MBF by conversion to higher boiling compounds, then distilling the phenol to separate phenol from higher boiling compounds. The phenol may be treated in known ways, such as by treatment with an amine, to reduce the level of acetol. The phenol containing a low level of acetol is contacted with a strong acid resin to reduce the level of MBF.

BEST MODE FOR CARRYING OUT THE INVENTION

The phenol product which can be purified in accordance with the method of the present invention has been obtained by decomposition of cumene hydroperoxide to form phenol and acetone as principal products, followed by distillation to remove the acetone which has a lower boiling point than phenol. We have now found that 2- and 3-methylbenzofuran (collectively or individually MBF) can be effectively and economically removed from phenol by treatment with an aromatic sulfonic acid resin or a solid superacid catalyst compound at moderate temperatures provided that acetol (hydroxyacetone), another phenol impurity, is absent or present in the phenol at low levels, for example in an amount not to exceed 260 ppm, preferably not to exceed 200 ppm, more preferably not to exceed 100 ppm, most preferably not to exceed 5 ppm. At higher concentrations of acetol, the effect of resin treatment decreases and becomes progressively less economically attractive.

Strong acid resins useful for this invention contain aromatic sulfonic acid groups and typically consist of granules of sulfonated crosslinked polystyrene. Such aromatic sulfonic acid resins are available commercially, for example Amberlyst ® 15 resin, a bead form sulfonic acid cation exchange resin available from Rohm and Haas. Additionally, solid superacid catalyst systems may be used. These systems have been developed as alternatives to liquid acid systems such as hydrofluoric acid used for petroleum acylation operations. Some are obtained from existing systems ($AlCl_3$, $SbF_5$, $SO_4^{2-}$ on a supporting substrate of $ZrO_2$ or $TiO_2$) by attaching existing strong acid constituents to oxide or salt substrates to immobilize the acid activity. Others are more novel heteropolyacids made from metal oxide clusters (tungsten and molybdenum). Representative catalysts are discussed in "Solid Superacid Catalysts," Makoto Misuno and Toshio Okuhara, *Chemtech*, November 1993. Solid superacid catalyst compounds are defined herein as those acid compounds with acid strength greater than that of 100% $H_2SO_4$.

The effectiveness of the treatment with resin increases with increasing temperature within the range of stability of the resin itself, for example within the range of 70° to 120° C., more preferably 80° to 110° C. Higher contact times are also more effective but increase the cost of the treatment. The contact of the phenol with the acid resin can be accomplished in known ways, such as by stirring the resin beads with the phenol, or by passing the phenol through a bed of acid resin, which may be the preferred commercial alternative. The effectiveness of temperature and contact time are demonstrated in the following examples. See example 1 for a definition of the unit of bed volume/hour, which for this invention is preferred to be 1 to 10, more preferably 2 to 6 bed volume/hour. In these examples analysis of 2-MBF was by conventional gas chromatography when present in concentrations of 1 ppm or greater. Below that concentration, liquid chromatography was performed using a non-polar, octadecylsilane column and a UV detector set at a wave length of 254 nm. Methanol/water was used as the eluent at ambient temperature at the constant composition of 90/10 by volume. Calculations of 2-MBF concentrations were based on comparisons of peak areas to calibration standards.

EXAMPLE 1

Phenol containing less than 1 ppm acetol and amounts of MBF as indicated in Table 1 under "inlet" was passed through a bed of acid resin (Amberlyst 15) at the rates and temperature indicated. Bed volume is a volume of phenol corresponding to the volume of the resin bed used. The unit bed volume/hour is inversely proportional to contact time. The results of analyses on outlet samples show that the treatment is more effective at higher temperature and lower bed volume/hr values (higher contact times). The results also show that MBF levels can be reduced to less than 0.1 ppm.

EXAMPLE 2

Phenol containing amounts of acetol and MBF as indicated under "inlet" in Table II was passed through a bed of acid resin (Amberlyst 15) at 4.0 bed volumes/hr. Samples were taken after the resin bed and analyzed. The results show that although acetol was removed by the treatment, to levels of less than 1 ppm, MBF could not be lowered to less than 4 ppm.

EXAMPLE 3

Phenol containing 20 ppm MBF and amounts of acetol of less than 1,200, and 500 ppm, respectively was passed through a bed of acid resin (Amberlyst 15) at 4 bed volumes/hour at different temperatures as shown on Table III. Samples were taken after the resin bed and analyzed. The results show that acetol hampers removal of MBF by the treatment and does so to a greater extent at higher temperatures. At 500 ppm acetol level and 110° C. there was no removal of MBF.

TABLE 1

Effect of temperature and contact time on removal of MBF from phenol containing less than 1 ppm acetol.

| T (°C.) | 2 Bed Volumes/hr. Inlet/Outlet | 4 Bed Volumes/hr. Inlet/Outlet | 6 Bed Volumes/hr. Inlet/Outlet |
| --- | --- | --- | --- |
| 65 | 20 ppm/<0.1 ppm | 23/3 | 24/14 |
| 80 | 16/<0.1 | 17/4 | 18/5 |
| 95 | 17/<0.1 | 18/<0.1 | 16/1.0 |
| 110 | 17/<0.1 | 16/<0.1 | 16/<0.1 |

TABLE II

Effect of acetol concentration on removal of MBF from phenol by acid resin at 4 bed volumes/hr.

| T (°C.) Bed | MBF Inlet/Outlet | Acetol Inlet/Outlet |
| --- | --- | --- |
| 80 | 20/4 ppm | 250/<1 ppm |
| 95 | 18/5 | 260/<1 |
| 95 | 18/5 | 250/<1 |
| 110 | 22/8 | 250/<1 |
| 116 | 25/11 | 260/<1 |
| 95 | 20/10 | 500/<1 |
| 110 | 25/25 | 500/<1 |

TABLE III

Effect of temperature and acetol level on MBF removal from phenol by acid resin at 4 bed volumes/hr.

| Acetol at Bed Inlet | MBF at Outlet | | |
| --- | --- | --- | --- |
| Temperature | 80° C. | 90° C. | 110° C. |
| <1 ppm | 4 | <0.1 | <0.1 |
| 200 | 4 | 5 | 8 |
| 500 | Not run | 10 | 25 |

What is claimed:

1. A process for the reduction of methylbenzofuran (MBF) impurities in phenol obtained from the decomposition product of cumene hydroperoxide comprising:
    treating the phenol to reduce the level of acetol to an amount not to exceed 260 ppm;
    contacting the phenol containing a low level of acetol with an aromatic sulfonic acid resin or a solid superacid catalyst compound at sufficient temperature and for sufficient time to reduce the level of MBF by conversion to higher boiling compounds; then
    distilling the phenol to separate phenol from higher boiling compounds.

2. The process of claim 1 wherein the phenol is treated to reduce the level of acetol to an amount not to exceed 200 ppm, then contacted with the acid or catalyst compound resin at a temperature of 70° to 120 ° C.

3. The process of claim 2 wherein the level of MBF is reduced to less than 10 ppm.

4. The process of claim 3 wherein the level of MBF is reduced to less than 1 ppm.

5. The process of claim 1 wherein the phenol is treated with an amine to reduce the level of acetol to an amount not to exceed 200 ppm, then contacted with an aromatic sulfonic acid resin in a resin bed at a temperature of 70° to 120° C. and at a rate of 1 to 10 bed volumes per hour.

6. The process of claim 5 wherein the level of MBF is reduced to less than 10 ppm.

7. The process of claim 6 wherein the level of MBF is reduced to less than 1 ppm.

8. The process of claim 1 wherein the phenol is treated with an amine to reduce the level of acetol to an amount not to exceed 10 ppm, then contacted with an aromatic sulfonic acid resin in a resin bed at a temperature of 70° to 120° C. and at a rate of 1 to 10 bed volumes per hour wherein the level of MBF is reduced to less than 1 ppm.

9. The process of claim 1 wherein the phenol is treated with an amine to reduce the level of acetol to an amount not to exceed 5 ppm, then contacted with an aromatic sulfonic acid resin in a resin bed at a temperature of 80° to 110° C. and at a rate of 2 to 6 bed volumes per hour wherein the level of MBF is reduced to less than 1 ppm.

* * * * *